(12) United States Patent
Wang-Lee

(10) Patent No.: US 6,591,424 B1
(45) Date of Patent: Jul. 15, 2003

(54) WELDER HELMET WITH FIXED AND MOVABLE FACE SHIELDS

(76) Inventor: Min-Young Wang-Lee, No. 473, Jong-Shan S. Rd., Yung-Kang City, Tainan Hsien (TW)

( * ) Notice: Subject to any disclaimer, the term of this patent is extended or adjusted under 35 U.S.C. 154(b) by 0 days.

(21) Appl. No.: 09/930,635

(22) Filed: Aug. 15, 2001

(51) Int. Cl.[7] ................................................. A42B 1/00
(52) U.S. Cl. .................................................... 2/8; 2/424
(58) Field of Search ............................. 2/424, 8, 9, 10, 2/11, 6.4, 6.5

(56) References Cited

U.S. PATENT DOCUMENTS

| | | | | |
|---|---|---|---|---|
| 2,762,049 A | * | 9/1956 | Herrick et al. | |
| 3,013,273 A | * | 12/1961 | Kamperin | |
| 3,419,907 A | * | 1/1969 | Zahn | |
| 4,856,109 A | * | 8/1989 | Desy et al. | |
| 4,888,825 A | * | 12/1989 | Hakala et al. | |
| 5,086,515 A | * | 2/1992 | Giuliano | |

FOREIGN PATENT DOCUMENTS

GB          2052244       *  1/1981

* cited by examiner

*Primary Examiner*—Rodney M. Lindsey
(74) *Attorney, Agent, or Firm*—Merchant & Gould P.C.

(57) ABSTRACT

A welder helmet includes a shield holder. A head set is disposed rearwardly of and is pivoted to left and right ends of the shield holder. A fixed face shield extends downwardly from the shield holder. A movable face shield is disposed frontwardly of the fixed face shield. A coupler unit couples the movable face shield on the shield holder to permit turning of the movable face shield away from the fixed face shield when the welder wishes to check a welded spot.

3 Claims, 7 Drawing Sheets

WELDER HELMET WITH FIXED AND MOVABLE FACE SHIELDS

BACKGROUND OF THE INVENTION

1. Field of the Invention

The invention relates to a welder helmet, more particularly to a welder helmet which is provided with fixed and movable face shields.

2. Description of the Related Art

A conventional welder helmet generally includes a head set that is adapted to be worn around the head of a welder, and a dark-colored face protective shield pivoted to the head set in such a manner that the face protective shield is disposed frontwardly of the welder in use, and is movable relative to the head set so as to be pivoted away from the welder's face when the welder wishes to check a welded spot.

It is noted that the face protective shield in the aforesaid conventional welder helmet is heavy due to a relatively large size requirement for covering an area from the forehead to the chin of the welder's face during use. As such, a relatively large force must be exerted in order to lift the protective shield away from the welder's face.

SUMMARY OF THE INVENTION

Therefore, the object of this invention is to provide a welder helmet with a simple structure and that can overcome the aforementioned disadvantage associated with the conventional welder helmet.

Accordingly, a welder helmet of the present invention includes a curved shield holder, a head set, a fixed face shield, a movable face shield, and a coupler unit. The curved shield holder defines front and rear sides, and has horizontally spaced apart left and right ends. The head set is disposed rearwardly of the shield holder, and is mounted pivotally to the left and right ends of the shield holder. The fixed face shield extends downwardly from the shield holder. The movable face shield is disposed frontwardly of the fixed face shield, and has an upper edge disposed adjacent to the shield holder. The coupler unit couples the movable face shield on the shield holder, and includes a pivotal member, a bracket, and a spring-biased limiting unit. The pivotal member is in the form of a hollow body that is fixed on and that extends outwardly and frontwardly from the front side of the shield holder to define a chamber therein, that has a front end stopper, and that is formed with a pair of diametrically opposing slots which extend rearwardly from the front end stopper. The bracket is fixed on the upper edge of the movable face shield and includes a looped portion that is hung on the hollow body and that has an engaging portion extending into the chamber and spanning the slots so as to permit turning of the movable face shield relative to the hollow body. The spring-biased limiting unit is mounted within the chamber, and is disposed rearwardly of the engaging portion for urging the engaging portion to abut against the front end stopper, thereby arresting unforced rotation of the movable face shield relative to the hollow body.

BRIEF DESCRIPTION OF THE DRAWINGS

Other features and advantages of this invention will become more apparent in the following detailed description of the preferred embodiment of this invention, with reference to the accompanying drawings, in which.

DETAILED DESCRIPTION OF THE PREFERRED EMBODIMENT

Figure 1:
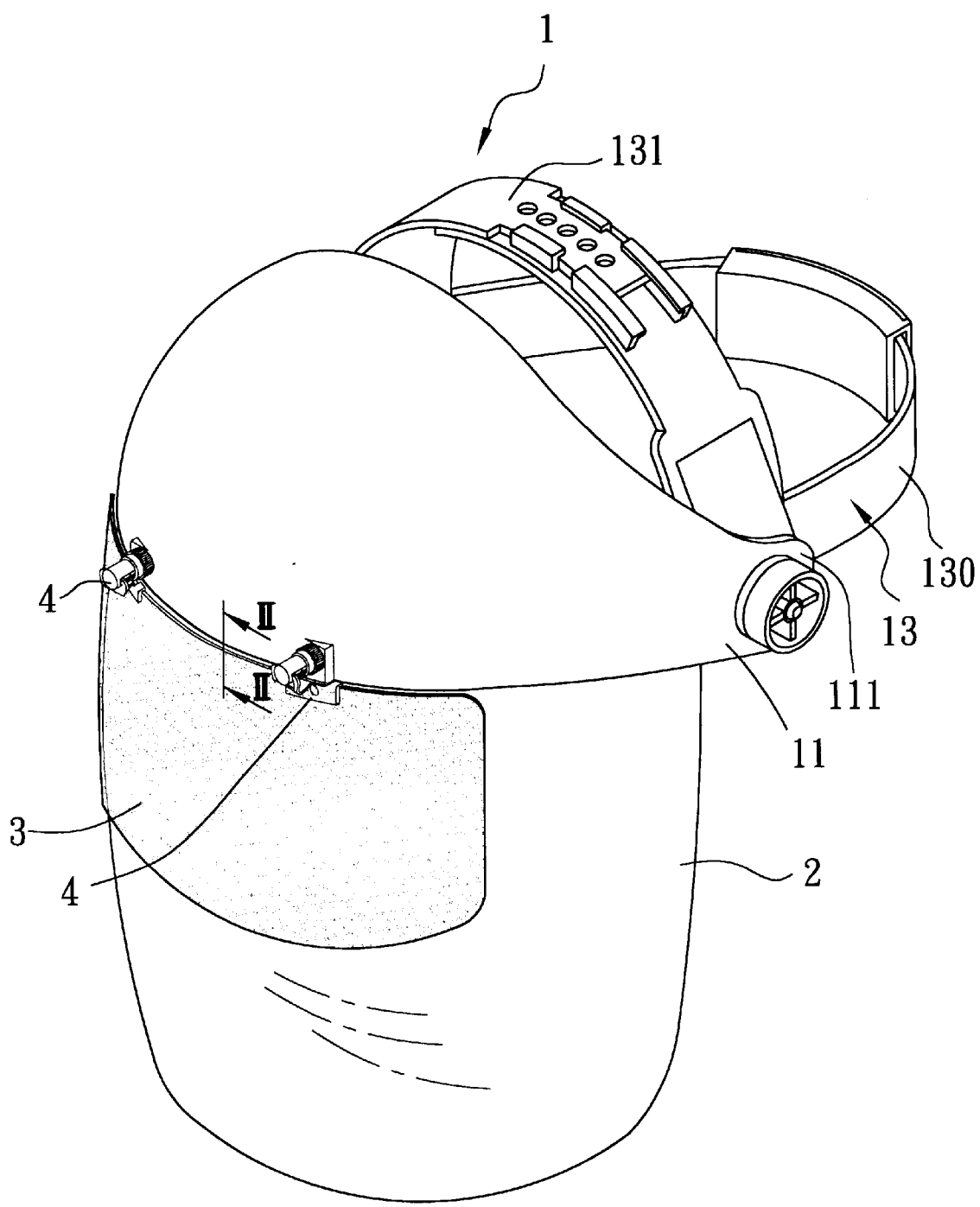
FIG. 1 is a perspective view of a preferred embodiment of a welder helmet according to the present invention.
Figure 2:
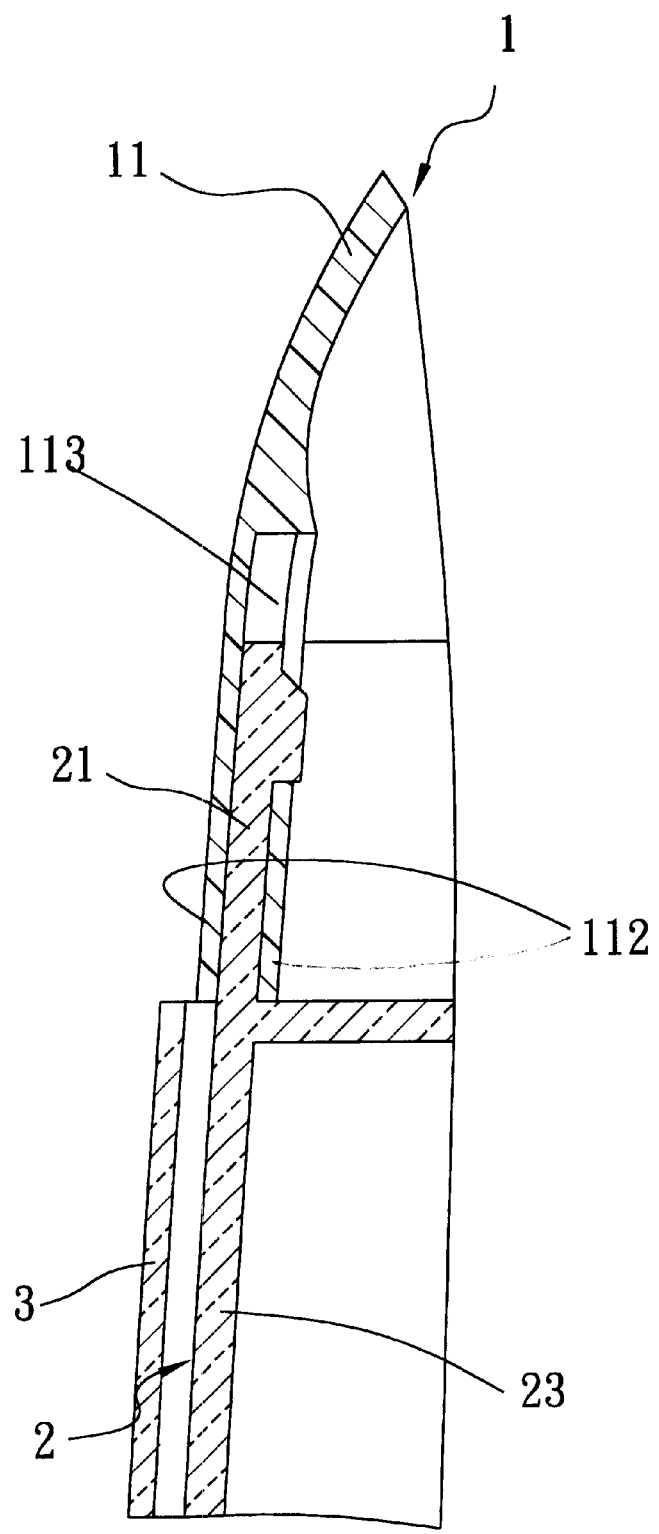
FIG. 2 is a fragmentary sectional view of the preferred embodiment taken along lines II—II in FIG. 1.
Figure 3:
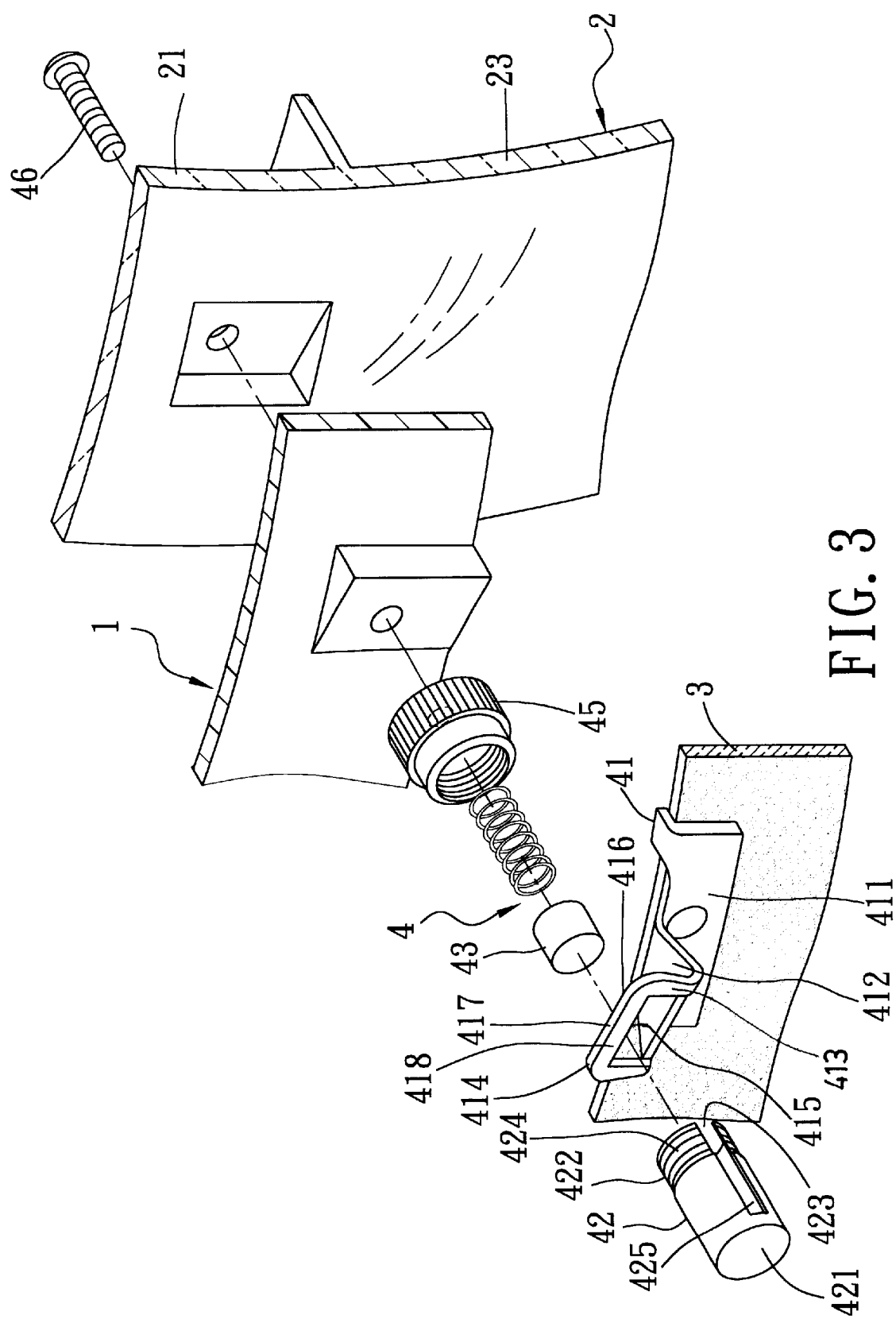
FIG. 3 is a fragmentary exploded perspective view illustrating how a movable face shield is mounted relative to a fixed face shield in the preferred embodiment.

Referring to FIGS. 1 to 3, the preferred embodiment of a welder helmet 1 according to the present invention is shown to include a curved shield holder 11, a head set 13, a transparent fixed face shield 2, a movable face shield 3, and a coupler unit 4 which couples the movable face shield 3 to the shield holder 11.

As illustrated, the curved shield holder 11 defines front and rear sides, and has horizontally spaced apart left and right ends 111, and two clamping plates 112 between which a shield-retention groove 113 is defined.

The head set 13 is disposed rearwardly of the shield holder 11, and is mounted pivotally to the left and right ends 111 of the shield holder 11.

The fixed face shield 2 has an upper portion 21 fittingly inserted into the shield-retention groove 113 of the shield holder 11, and a lower portion 23 which extends downwardly from the shield holder 11.

The movable face shield 3 is generally dark-colored and is disposed frontwardly of the fixed face shield 2, and has an upper edge disposed adjacent to the shield holder 11.

The coupler unit 4 includes a pivotal member 42, a bracket 41, a spring-biased limiting unit 43. The pivotal member 42, in the form of a hollow body 422, is fixed on and extends outwardly and frontwardly from the front side of the shield holder 11 to define a chamber 423 therein. The hollow body 422 has a front end stopper 421 and is formed with a pair of diametrically opposing slots 425 which extend rearwardly from the front end stopper 421. The bracket 41 has a lower part 411 fixed on the upper edge of the movable face shield 3, and includes a looped portion 413 that is hung on the hollow body 422 and that has an engaging portion 414 extending into the chamber 423 and spanning the slots 425 so as to permit turning of the movable face shield 3 relative to the hollow body 422. The spring-biased limiting unit 43 is mounted within the chamber 423 and is disposed rearwardly of the engaging portion 414 for urging the latter to abut against the front end stopper 421 of the hollow body 422, thereby arresting unforced rotation of the movable face shield 3 relative to the hollow body 422.

Figure 4:
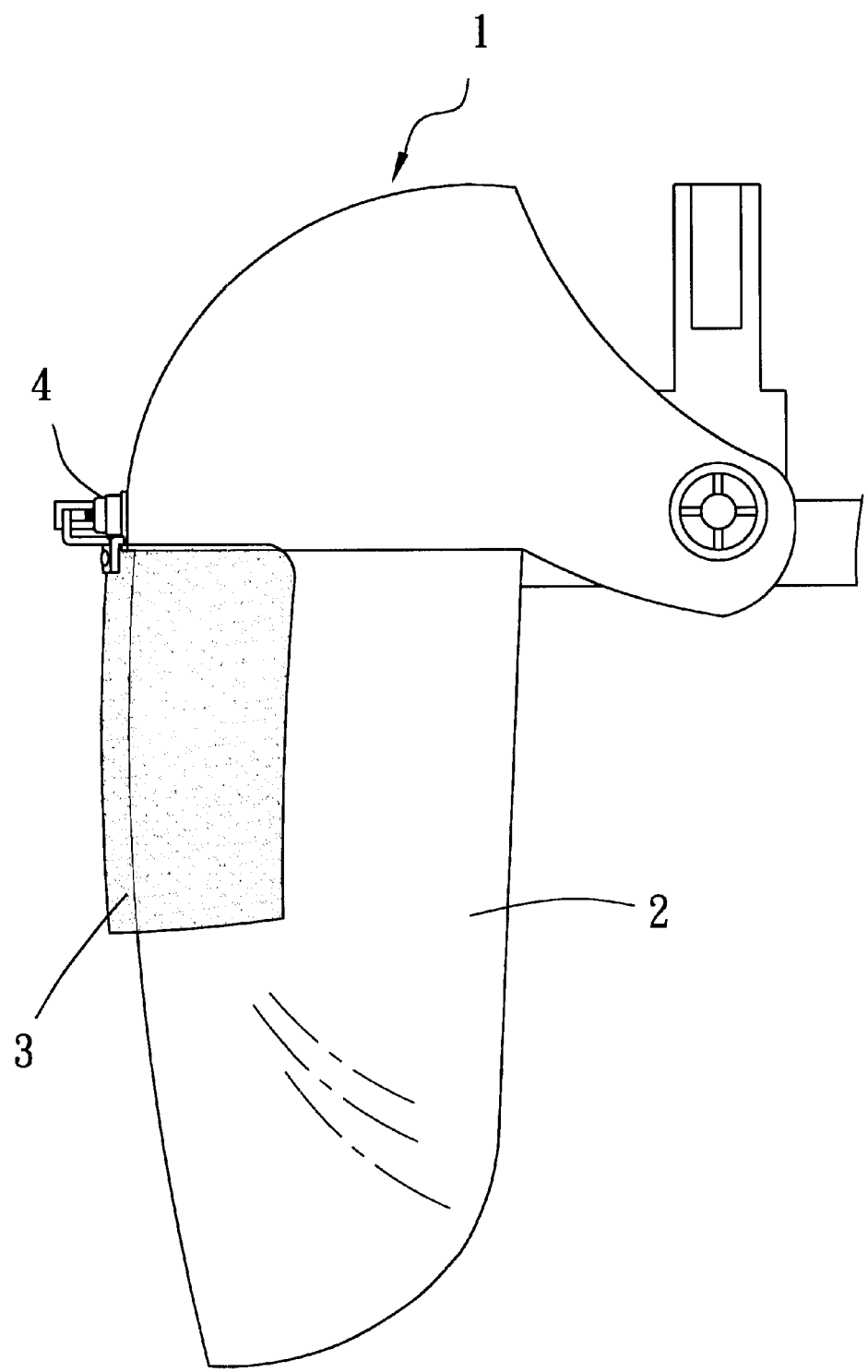
FIG. 4 is a schematic side view of the preferred embodiment during use.
Figure 5:
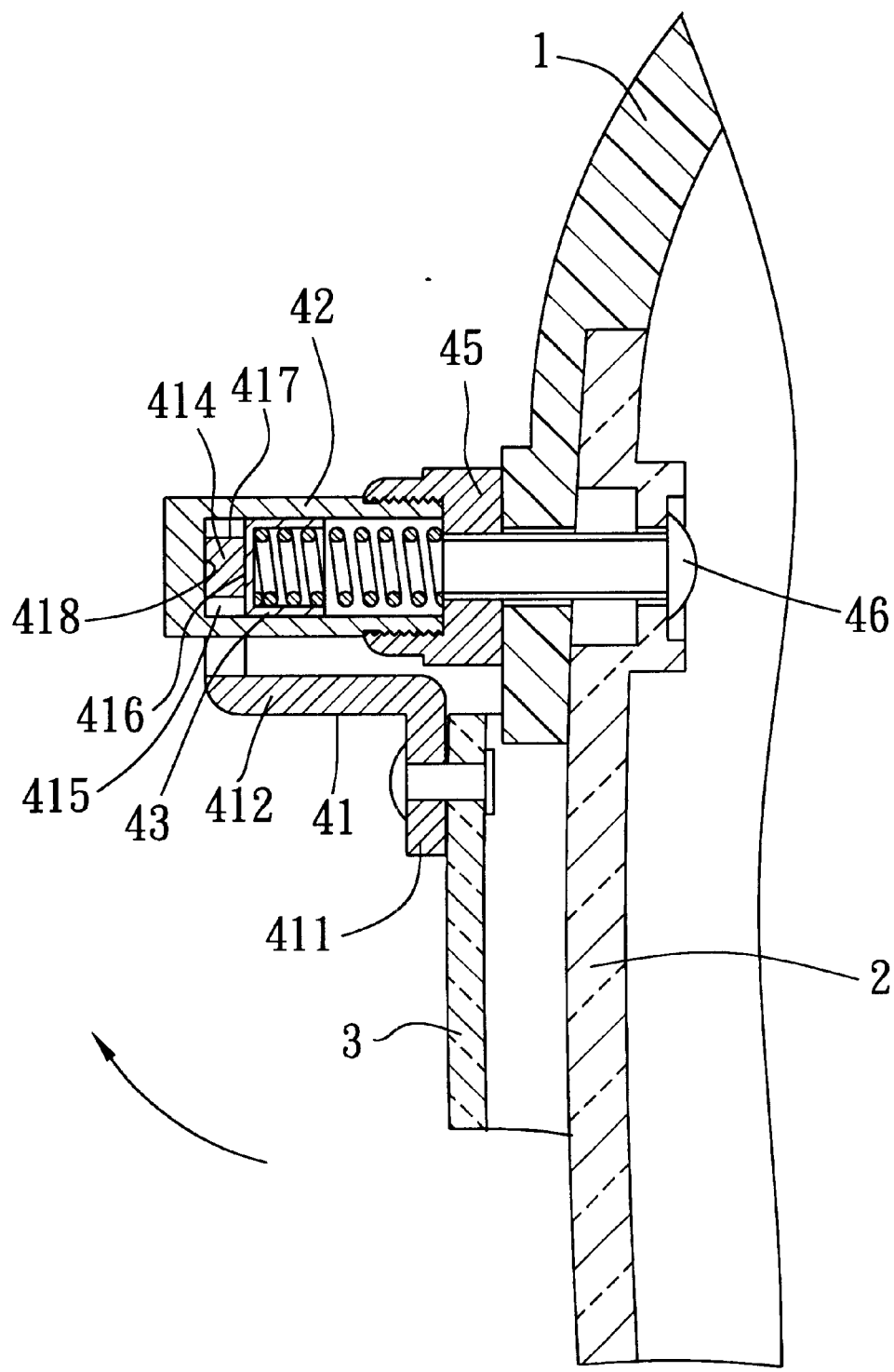
FIG. 5 is a fragmentary sectional side view of the preferred embodiment, illustrating a coupling unit that couples the movable face shield relative to the fixed face shield.
Figure 6:
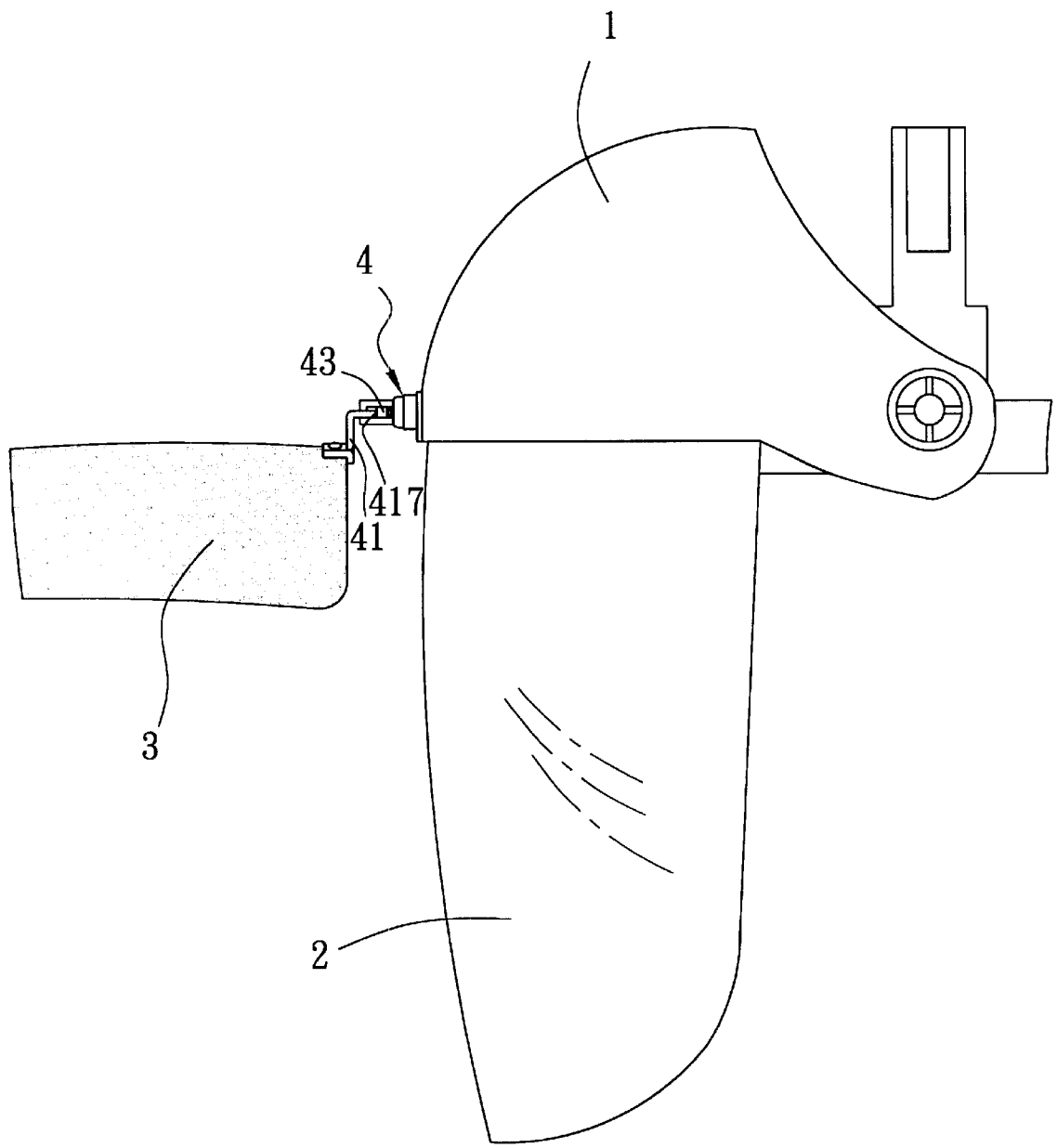
FIG. 6 is a schematic side view of the preferred embodiment, illustrating how the movable face shield is moved relative to the fixed face shield from a first position to a second position.

The engaging portion 414 has a generally rectangular cross-section, and has front and rear abutment faces 418,416 which extend in a direction transverse to a length of the hollow body 422 and which respectively abut against the front end stopper 421 of the hollow body 422 and the spring-biased limiting unit 43 when the movable face shield 3 is disposed at a first position parallel to the fixed face shield 2, as best shown in FIG. 4, and top and bottom abutment faces 417,415 which interconnect the front and rear abutment faces 418,416 and which respectively abut against the spring-biased limiting unit 43 and the front end stopper 421 when the movable face shield 3 is turned against urging action of the spring-biased limiting unit 43 from the first position of FIG. 4 to a second position perpendicular to the fixed face shield 2, as best shown in FIG. 6.

Figure 7:
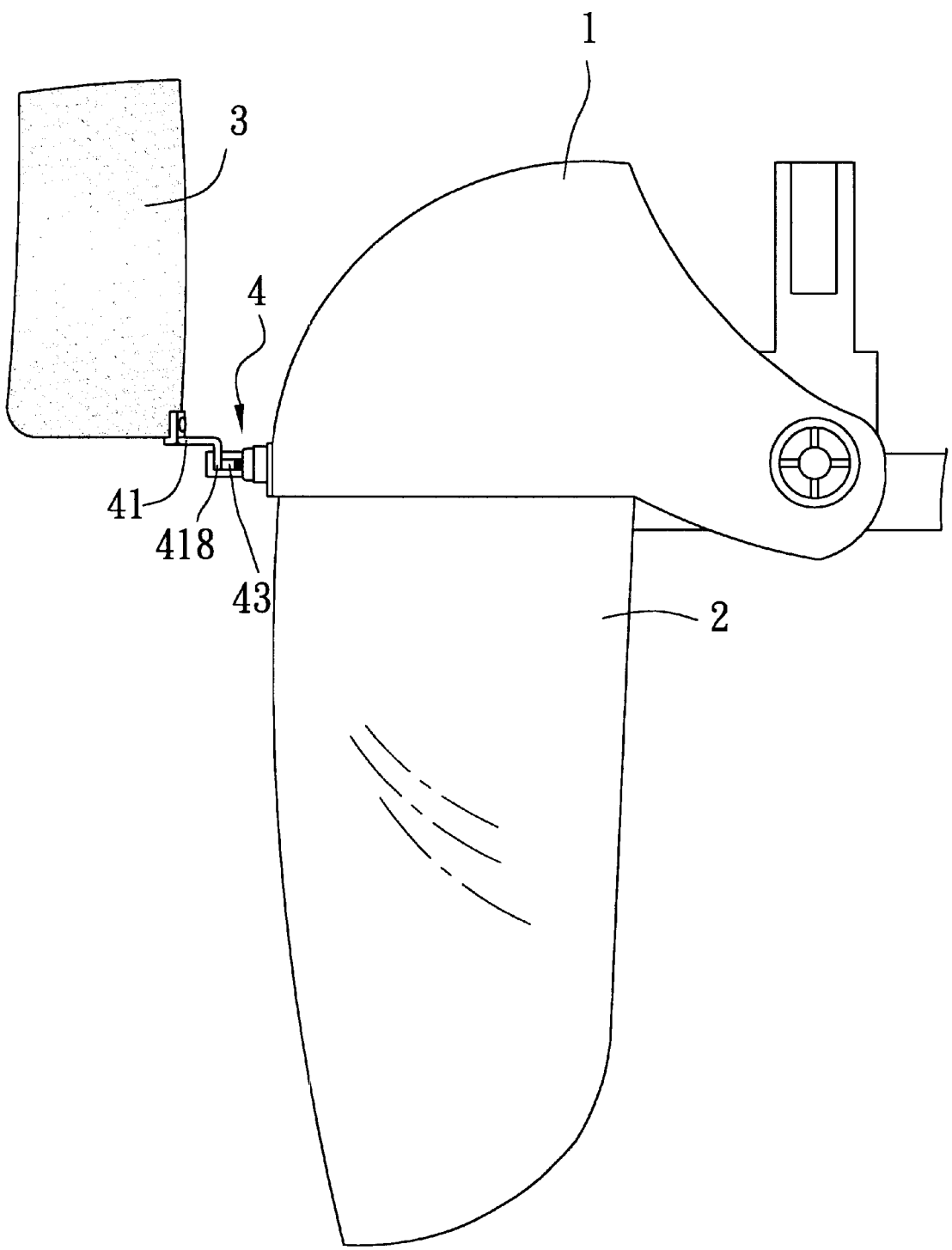
FIG. 7 is a schematic side view of the preferred embodiment, illustrating how the movable face shield is moved relative to the fixed face shield from the second position to a third position.

The movable face shield 3 can be further turned against urging action of the spring-biased limiting unit 43 from the second position of FIG. 6 to a third position shown in FIG. 7, during which the engaging portion 414 rotates in the slots 425 such that the front and rear abutment faces 418,416 respectively abut against the spring-biased limiting unit 43 and the front end stopper 421 of the hollow body 422.

The coupler unit 4 further includes a mounting seat 45 fixed on the front side of the shield holder 1 via a screw 46. The hollow body 422 has a distal threaded portion 424 threadedly engaging the mounting seat 45 to confine the chamber 423 therebetween.

The head set 13 includes a flexible ring-shaped band 130 that has first and second free end sections which overlap and which are movable toward and away from each other so as to adjust the size thereof, and two head straddling straps 131 which extend upwardly and inwardly from the ring-shaped band 130 and which have distal strap sections that are disposed in an overlapping manner and that are movable toward and away from each other. Since the features of the present invention does not reside in the particular configuration of the head set 13, a detailed description of the same is omitted herein for the sake of brevity.

Preferably, the bracket 41 includes a projection 412 which extends frontwardly from the lower part 411 to facilitate turning of the looped portion 413 on the hollow body 422.

Note that the movable face shield 3 has a relatively small size as compared to the fixed face shield 2 and is adapted to cover only the upper part of the welder's face. As such, the movable face shield 3 is relatively light in weight. Accordingly, only a relatively small force is required to lift the movable face shield 3 away from the fixed face shield 2 when the welder wishes to check a welded spot.

With this invention thus explained, it is apparent that numerous modifications and variations can be made without departing from the scope and spirit of this invention. It is therefore intended that this invention be limited only as indicated in the appended claims.

I claim:

1. A welder helmet comprising:
   a curved shield holder defining front and rear sides, and having horizontally spaced apart left and right ends;
   a head set disposed rearwardly of said shield holder and mounted pivotally to said left and right ends;
   a fixed face shield extending downwardly from said shield holder;
   a movable face shield disposed frontwardly of said fixed face shield, and having an upper edge disposed adjacent to said shield holder; and
   a coupler unit coupling said movable face shield on said shield holder, and including a pivotal member in the form of a hollow body that is fixed on and that extends outwardly and frontwardly from said front side of said shield holder to define a chamber therein, and that has a front end stopper and that is formed with a pair of diametrically opposing slots extending rearwardly from said front end stopper, a bracket which is fixed on said upper edge of said movable face shield and which includes a looped portion that is hung on said hollow body and that has an engaging portion extending into said chamber and spanning said slots so as to permit turning of said movable face shield relative to said hollow body, and a spring-biased limiting unit which is mounted within said chamber and which is disposed rearwardly of said engaging portion for urging said engaging portion to abut against said front end stopper, thereby arresting unforced rotation of said movable face shield relative to said hollow body.

2. The welder helmet as defined in claim 1, wherein said engaging portion has a generally rectangular cross-section, and defines front and rear abutment faces which extend in a direction transverse to a length of said hollow body and which respectively abut against said front end stopper of said hollow body and said spring-biased limiting unit when said movable face shield is disposed at a first position parallel to said fixed face shield, and top and bottom abutment faces which interconnect said front and rear abutment faces and which respectively abut against said spring-biased limiting unit and said front end stopper when said movable face shield is turned against urging action of said spring-biased limiting unit from said first position to a second position perpendicular to said fixed face shield.

3. The welder helmet as defined in claim 2, wherein said coupler unit further includes a mounting seat fixed on said front side of said shield holder, said hollow body threadedly engaging said mounting seat to confine said chamber therebetween.

* * * * *